United States Patent [19]

Dixon et al.

[11] Patent Number: 4,701,322

[45] Date of Patent: Oct. 20, 1987

[54] CONDITIONING SHAMPOO

[75] Inventors: Thomas J. Dixon, Cincinnati; Vernon A. Uchtman, Green Hills, both of Ohio

[73] Assignee: The Procter & Gamble Company, Cincinnati, Ohio

[21] Appl. No.: 706,898

[22] Filed: Feb. 28, 1985

Related U.S. Application Data

[63] Continuation of Ser. No. 142,297, Apr. 21, 1980.

[51] Int. Cl.⁴ ............................................. A61K 7/06
[52] U.S. Cl. ......................................... 424/70; 132/7
[58] Field of Search ......................................... 424/70

[56] References Cited

U.S. PATENT DOCUMENTS

| | | | |
|---|---|---|---|
| 2,674,580 | 4/1954 | Henkin | 424/70 |
| 2,879,231 | 3/1954 | Allen | 424/70 |
| 2,900,307 | 8/1959 | Wei | 424/70 |
| 2,928,772 | 3/1960 | Anderson | 424/70 |
| 2,950,255 | 8/1960 | Goff | 424/70 |
| 3,261,753 | 7/1966 | Gotte et al. | |
| 3,406,238 | 10/1968 | Freysimuth et al. | |
| 3,590,122 | 6/1971 | Roberts et al. | 424/70 |
| 3,886,277 | 5/1975 | Randebrock | |

FOREIGN PATENT DOCUMENTS

| | | | |
|---|---|---|---|
| 874627 | 8/1961 | United Kingdom | 424/70 |
| 979292 | 1/1965 | United Kingdom | |

OTHER PUBLICATIONS

Redgrove, Hair Dyes and Hair Dyeing, 1939, pp. 117–121.
Pharmaceutical Formulas, vol. II, The Chemist and Druggist, London, Great Britain, 1946, pp. 241–247.
Miall, A New Dictionary of Chemistry, Interscience Pub., Inc., New York, 1961, p. 391.
1972 Cosmetic Formulary, Emery Products for Cosmetics & Drug Industries, p. B 25.

Primary Examiner—Dale R. Ore
Attorney, Agent, or Firm—Richard C. Witte; John V. Gorman; Douglas C. Mohl

[57] ABSTRACT

A conditioning shampoo containing as the conditioning agent a saturated, straight chain fatty acid having from about 14 to about 18 carbon atoms.

8 Claims, No Drawings

4,701,322

CONDITIONING SHAMPOO

CROSS-REFERENCE TO RELATED APPLICATION

This is a continuation of application Ser. No. 142,297, filed on Apr. 21, 1980.

TECHNICAL FIELD

The present invention relates to conditioning shampoos which contain a saturated, straight chain fatty acid having from about 14 to about 18 carbon atoms as the conditioning agent.

BACKGROUND ART

Human hair becomes soiled due to its contact with the surrounding atmosphere and, to a greater extent, from sebum secreted by the head. The build-up of sebum causes the hair to have a dirty feel and an unattractive appearance. The soiling of the hair necessitates it being shampooed with frequent regularity.

Shampooing the hair cleans by removing excess soil and sebum. However, the shampooing process has disadvantages in that the hair is left in a wet, tangled, and generally unmanageable state. The latter problem is also prevalent with dry hair. A variety of approaches have been developed to alleviate the after-shampoo problems. These have ranged from the inclusion of hair conditioning aids such as soaps, polymers and cationic agents in shampoos to post-shampoo application of hair conditioners, i.e. hair rinses. Difficulties associated with the use of conditioning aids in shampoos have been compatibility problems and a greasy feels on the just-washed hair.

Hair rinses typically work by depositing a polymeric film or other material onto the hair. However, such solutions to a very prevalent problem have not been fully satisfactory. For one thing, hair rinses are generally liquid in nature and must be applied in a separate step following the shampooing, left on the hair for a length of time, and rinsed with fresh water. This, of course, is time consuming and is not convenient. The results obtained in this manner also have not been fully satisfactory due to the difficulties associated with the deposition and retention on the hair of the hair conditioning aid. The inclusion of suitable conditioning agents in a shampoo therefore has certain attractive features.

As indicated above, many attempts have been made to incorporate conditioning agents into shampoos. One reference disclosing a conditioning shampoo employing a soap in U.S. Pat. No. 3,808,329, Apr. 30, 1974 to Bolich et al. The disclosed shampoos have a pH of 7.0 to 8.4 and contain a polyoxyethylene ester to create a milder shampoo. Another reference is U.S. Pat. No. 3,590,122, June 29, 1971 to Roberts et al wherein shampoos containing fatty acids which are partially neutralized and having a pH of 5.0 to 8.5 are disclosed. The fatty acids are branched and a preferred acid is isostearic acid.

While the above references disclose using soaps and soaps mixed with unsaponified fatty acids, they are not suggestive of compositions wherein fatty acids are present in a shampoo having a pH of about 3.0 to about 5.5. Furthermore, they do not suggest the advantages of conditioning with a fatty acid rather than soap.

It is an object of the present invention to provide a superior conditioning shampoo composition.

It is a further object of the present invention to provide a superior hair conditioning shampoo composition comprising a saturated, straight chain fatty acid having from about 14 to about 18 carbon atoms, an anionic surfactant and having a pH of from about 3.0 to about 5.5

A still further object of the present invention is to provide a superior method for cleaning and conditioning hair.

These and other objects of the invention will become apparent from the description to follow.

As used herein, all percentages and ratios are by weight unless otherwise indicated.

DISCLOSURE OF INVENTION

The present invention relates to conditioning shampoos containing as the conditioning agent a saturated, straight chain fatty acid having from about 14 to about 18 carbon atoms. Such compositions generally comprise:

A. from about 10% to about 26% of a synthetic anionic surfactant;
B. from about 1% to about 3% of fatty acid; and
C. the remainder water wherein said composition has a pH of from about 3.0 to about 5.5.

DETAILED DESCRIPTION OF THE INVENTION

The conditioning shampoo compositions of the present invention comprise as noted above an anionic surfactant, a fatty acid and water. Suitable surfactants, fatty acids, pH adjustment agents and optional ingredients are discussed in detail below.

Surfactant

One essential component of the conditioning shampoos herein is a surfactant. The term "surfactant" as used herein is intended to denote a synthetic anionic surfactant.

Anionic surfactants suitable for use herein can be exemplified by the salts of organic sulfuric reaction products having in their molecular structure an alkyl radical containing from 8–22 carbon atoms and a sulfonic acid or sulfuric acid ester radical (included in the term alkyl is the alkyl portion of higher acyl radicals). Preferred are the ammonium, sodium, potassium or triethanolamine alkyl sulfates, especially those obtained by sulfating the higher alcohols ($C_8$–$C_{18}$ carbon atoms); sodium coconut oil fatty acid monoglyceride sulfates and sulfonates; ammonium, triethanolamine, sodium or potassium salts of sulfuric acid esters of the reaction product of 1 mole of a higher fatty alcohol e.g., tallow or coconut oil alcohols) and 1 to 12 moles of ethylene oxide; sodium or potassium salts of alkyl phenol ethylene oxide ether sulfates with 1 to 10 units of ethylene oxide per molecule and in which the alkyl radicals contain from 8 to 12 carbon atoms; and sodium alkyl glyceryl ether sulfonates.

The more preferred surfactants for use in the present compositions include ammonium or sodium lauryl sulfate and ammonium or sodium lauryl ether (3 ethylene oxide groups) sulfate or combinations thereof. Ammonium lauryl sulfate is most preferred as the surfactant for the present compositions. The surfactant level is between 10% and 26%, preferably between 13% and 20%.

Fatty Acid

The conditioning agent of the present composition, a saturated, straight chain fatty acid having from about 14 to about 18 carbon atoms, is present at a level of from about 1% to about 3%. Preferably, the level is from about 1% to about 2%.

Suitable fatty acids include myristic acid, palmitic acid, stearic acid and mixtures thereof. The preferred fatty acid is palmitic acid.

Aqueous Carrier

The shampoos herein are preferably in the form of liquids or creams in which water is the principal diluent. The level of water in the compositions is typically from about 35% to about 89% by weight.

pH Adjustment Agent

The pH of the shampoo compositions herein should lie in the range of about 3.0 to about 5.5, preferably in the range of about 4.5 to about 5.0. The pH is kept in the acidic range to maintain the fatty acid in an unsaponified state. Suitable pH adjustment agents include citric acid, phosphoric acid, succinic acid and a sodium citrate/citric acid combination among many other.

Optional Components

The conditioning shampoos herein can contain a variety of non-essential optional ingredients suitable for improving such compositions in a variety of ways. Such conventional optional ingredients are well known to those skilled in the art, e.g. preservatives such as benzyl alcohol, methyl paraben, propyl paraben and imidiazolidinyl urea; thickeners and viscosity modifiers such as coconut ethanol amide, sodium chloride, ammonium chloride, sodium sulfate, carboxymethyl cellulose, methylcellulose, polyvinyl alcohol, and ethyl alcohol; suspending agents such as magnesium/aluminum silicate; perfumes; dyes; opacifiers such as behenic acid, ethylene glycol distearate and calcium stearate; sequestering agents such as disodium ethylenediamine tetraacetate; and perfumes. If present, such agents individually generally comprise from about 0.01% to 5.0% by weight of the composition.

Surfactants, other than anionics, can also be added as optional components to the present compositions. The optional surfactants may be selected from any of the other types of surfactants but the preferred types are nonionics and amphoterics.

Method of Manufacture

The shampoo compositions of the present invention are made using mixing techniques which are well known in the art. A method of making the present invention is shown in the examples which follow.

Composition Use

In its method aspect, the present invention comprises a method of shampooing the hair by contacting the hair with an amount of the shampoo compositions herein which is effective to clean and condition the hair and rinsing the shampoo from the hair. An effective amount for any individual will depend upon variable factors such as length of the hair, thickness of the hair, amount of soil present, level of surfactant in the shampoo composition, etc. Generally, an effectie amount will be from about 5 to about 40 grams per use.

The following examples will illustrate the invention, but are not intended to be in any way limiting thereof.

EXAMPLE I

A typical shampoo composition of the present invention has the following formula:

| Ingredient | Wt. % |
| --- | --- |
| Distilled Water | 80.16 |
| Ammonium Lauryl Sulfate | 15.12 |
| Palmitic Acid | 1.10 |
| Coconut Monoethanolamide | 1.00 |
| Ethylene Glycol Distearate | 1.00 |
| Citric Acid | 0.50 |
| Sodium Hydroxide | 0.30 |
| Ammonium Chloride | 0.25 |
| Fragrance | 0.25 |
| Color (1% Sol) | 0.02 |
| Methyl Paraben | 0.20 |
| Propyl Paraben | 0.10 |
| TOTAL | 100.00 |

EXAMPLE II

Another typical composition of the present invention is as follows:

| Ingredient | Wt. % |
| --- | --- |
| Distilled Water | 70.58 |
| Sodium Lauryl Ether (3EO) Sulfate | 25.00 |
| Palmitic Acid | 1.10 |
| Coconut Monoethanolamide | 1.00 |
| Ethylene Glycol Distearate | 1.00 |
| Citric Acid | 0.50 |
| Ammonium Chloride | 0.25 |
| Fragrance | 0.25 |
| Color (1% Sol) | 0.02 |
| Methyl Paraben | 0.20 |
| Propyl Paraben | 0.10 |
| TOTAL | 100.00 |

Freshly washed hair has less of a tendency to "fly away" when combed after drying if the compositions of Examples I and II are used rather than the same compositions without palmitic acid to wash the hair.

EXAMPLE III

A method which can be used to make the preceding exemplary compositions of the present invention is as follows:
1. The distilled water is heated to 120°–130° F.
2. The methyl and propyl parabens are slowly added to the water and the mixture is agitated vigorously until both are completely dissolved.
3. The sodium hydroxide is added (if present).
4. The batch is heated until the temperature reaches 130° F. at which temperature the palmitic acid is added. The batch is mixed until the palmitic acid is completely solubilized.
5. The coconut monoethanolamide is added and agitation is maintained at a moderate speed to minimize foaming.
6. The ethylene glycol distearate is added and the batch temperature is allowed to increase to 145°–150° F.
7. Finally the color and the perfume are added and the total patch is allowed to mix for an additional 10 minutes before processing.

What is claimed is:
1. A shampoo composition consisting essentially of
  (a) from about 10% to about 26% of a synthetic anionic surfactant;
  (b) from about 1% to about 3% of a saturated, straight chain fatty acid selected from the group consisting of palmitic acid, myristic acid and mixtures thereof; and

(c) water, wherein said composition has a pH of from about 3.0 to about 5.5.

2. A shampoo composition according to claim 1, wherein the surfactant is selected from the group consisting of ammonium lauryl sulfate, sodium lauryl sulfate, ammonium lauryl ether sulfate, sodium lauryl ether sulfate and mixtures thereof.

3. A shampoo composition according to claim 2 wherein the pH is from about 4.5 to about 5.0.

4. A shampoo composition according to claim 3 wherein the fatty acid is palmitic acid and is present in an amount of from about 1.0% to about 1.5%.

5. A shampoo composition according to claim 4 wherein the surfactant is ammonium lauryl sulfate.

6. A shampoo composition according to claim 5 wherein citric acid is used to achieve the desired pH.

7. A method of cleaning and conditioning hair comprising wetting the hair with water, applying from about 5 to about 40 grams of the shampoo composition according to claim 1, working the shampoo through the hair, rinsing the shampoo from the hair and drying the hair.

8. The method according to claim 7 wherein the shampoo composition is the shampoo of claim 5.

* * * * *